(12) United States Patent
Maddahi et al.

(10) Patent No.: US 10,813,877 B2
(45) Date of Patent: *Oct. 27, 2020

(54) ORAL CARE PRODUCTS AND METHODS

(71) Applicant: MGE HOLDINGS LLC, Beverly Hills, CA (US)

(72) Inventors: Kourosh Maddahi, Beverly Hills, CA (US); Hessam Nowzari, Beverly Hills, CA (US)

(73) Assignee: Oral Health Innovations, LLC, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/850,655

(22) Filed: Dec. 21, 2017

(65) Prior Publication Data

US 2018/0333348 A1    Nov. 22, 2018

Related U.S. Application Data

(60) Provisional application No. 62/552,650, filed on Aug. 31, 2017, provisional application No. 62/465,536, filed on Mar. 1, 2017, provisional application No. 62/437,100, filed on Dec. 21, 2016.

(51) Int. Cl.

| | |
|---|---|
| *A61K 8/96* | (2006.01) |
| *A61K 8/92* | (2006.01) |
| *A61K 8/25* | (2006.01) |
| *A61K 8/34* | (2006.01) |
| *A61K 8/46* | (2006.01) |
| *A61K 8/9794* | (2017.01) |
| *A61Q 11/00* | (2006.01) |

(52) U.S. Cl.
CPC ............... *A61K 8/965* (2013.01); *A61K 8/25* (2013.01); *A61K 8/345* (2013.01); *A61K 8/466* (2013.01); *A61K 8/922* (2013.01); *A61K 8/9794* (2017.08); *A61Q 11/00* (2013.01)

(58) Field of Classification Search
None
See application file for complete search history.

(56) References Cited

U.S. PATENT DOCUMENTS

| | | | |
|---|---|---|---|
| 5,424,059 A * | 6/1995 | Prencipe | A61K 8/347 424/49 |
| 5,900,320 A | 5/1999 | Cutler | |
| 8,715,625 B1 * | 5/2014 | Rokitowski | A61Q 11/00 424/401 |

FOREIGN PATENT DOCUMENTS

| | | | | |
|---|---|---|---|---|
| KR | 20130027751 A * | 3/2013 | | |
| WO | WO-2012004782 A2 * | 1/2012 | | A23L 3/358 |

OTHER PUBLICATIONS

American Dental Association monograph on toothpaste. Downloaded Nov. 24, 2018 from https://www.ada.org/en/member/oral-health-topics/toothpastes (Year: 2018).*

"Dr. Kourosh Maddahi Launches New Oral Essentials Toothpaste," dated Jun. 6, 2016, downloaded Nov. 24, 2018 from:https://globenewswire.com/news-release/2016/06/06/846389/0/en/Dr-Kourosh-Maddahi-Launches-New-Oral-Essentials-Toothpaste-in-Original-and-Whitening-Formulas.html (Year: 2016).*

Natural remedies for oral health (from the blog of Ally C-ell, downloaded Nov. 24, 2018 from the Wayback Machine, dated Aug. 16, 2014 at https://web.archive.org/web/20140816204631/http://www.nipnoos.com/natural-remedies-for-oral-health/ (Year: 2014).*

Machine translation of KR 20130027751 (A) from Espacenet (Year: 2018).*

Dinghra, Oral Diseases, vol. 20, pp. 245-267 (2014).

* cited by examiner

*Primary Examiner* — Michael P Cohen

(74) *Attorney, Agent, or Firm* — Louis C. Paul (57) ABSTRACT

Oral care compositions consisting essentially of a Sea Salt, at least one essential oil, xylitol, and preferably, aloe vera juice and uses of such compositions to whiten teeth, reduce sensitivity of teeth/gums, and reduce xerostomia. In preferred embodiments directed to teeth whitening and xerostomia, the compositions also include coconut oil. Delivery systems for whitening teeth comprised of a strip formed be combining (i) one or a combination of teeth whitening ingredients selected from Dead Sea Salt, *Cocos Nucifera* (Coconut) Oil, *Citrus Limon* (Lemon) Peel Oil, and *Salvia Officinalis* (Sage) Oil and (ii) one or more gelling/thickening agents, wherein the strip is conformable to teeth surfaces and to interstitial spaces between teeth, without permanent deformation thereof, and is removably attached to a release liner. The strips may also contain one or more peroxides, metal chlorites, perborates, percarbonates, and peroxyacids.

10 Claims, 1 Drawing Sheet

ORAL CARE PRODUCTS AND METHODS

FIELD OF INVENTION

The present invention relates to compositions and methods for improving the appearance and health of teeth and gums with oral care products containing naturally-derived ingredients.

BACKGROUND OF INVENTION

The therapeutic and medicinal benefits of Dead Sea salts have been reported in the scientific literature, typically in connection with diseases of the skin and joints. See, e.g., Uriel Katz, Yehuda Shoenfeld, Varda Zakin, Yaniv Sherer, Shaul Sukenik, "Scientific Evidence of the Therapeutic Effects of Dead Sea Treatments: A Systematic Review, Seminars in Arthritis and Rheumatism," Vol. 42, No. 2 (October 2012), pp. 186-200, citing Z. Even-Paz, J. Shani, "The dead sea and psoriasis: Historical and geographic background," Int J Dermatol, Vo. 28, No. 1 (1989), pp. 1-9 (345 g of mineral per liter (34.5% or 34.5 g/100 mL); Id. citing, S. Sukenik, D. Flusser, S. Codish, M. Abu-Shakra "The Dead Sea—a unique resort for patients suffering from joint diseases," Harefuah, Vol. 149, No. 3 (2010), pp. (175-179)(180 to 215 g of mineral per liter). Dan Buskila, Mahmoud Abu-Shakra, Lily Neumann, Lisa Odes, Evgeny Shneider, Daniel Flusser, Shaul Sukenik, "Balneotherapy for Fibromyalgia at the Dead Sea," Rheumatol Int, Vol. 20 (2001), pp. 105-108.

The water of the Dead Sea is concentrated salts other than NaCl—including, but not limited to, $MgCl_2$, $CaCl_2$), KCl, and $MgBr_2$. Among the separate ions present in the Dead Sea water are, chloride (212.4 g/l), magnesium (40.65 g/l), sodium (39.15 g/l), calcium (16.86 g/l), potassium (7.26 g/l), bromide (5.12 g/l), sulfate (0.47 g/l), and bicarbonate (0.22 g/l). See, e.g., I. L. Schamberg, "Treatment of psoriasis at the Dead Sea," Int J Dermatol, Vol. 17, No. 6 (1978), pp. 524-525; Paz and Shani, supra.

European Patent Application EP1074245A2 discloses use of mineral salt, in particular Dead Sea salts, as an active ingredient in a mouthwash to "assist in combatting bacteria and gum irritation and inflammation"

Essential oils have been used for the treatment of a variety of ailments since ancient times. The safety and efficacy of essential oils in dentistry have been reported in numerous clinical studies. See, e.g., Namrata Dagli, Rushabh Dagli, 1 Rasha Said Mahmoud, and Kusai Baroudi, "Essential oils, their therapeutic properties, and implication in dentistry: A Review" J Int Soc Prev Community Dent. Vol. 5, No. 5 (2015), pp. 335-340.

The safety and potential for adverse effects from synthetic ingredients, not only for humans but also larger ecosystem, have long been of concern. These issues were brought to the forefront by Rachel Carson, in her 1962 book, *Silent Spring*, which focused on the impact of pesticides, in particular DDT, on birds. A decade later, in 1973, the United States banned DDT. In that same year, manufacturers and producers of health foods and products began organic certification. Two years later, in 1975, Tom's of Maine introduced what it claimed to be the first mass-marketed "natural" toothpaste. The ensuing decades saw an explosive growth in demand for natural and organic products grew. By 1990, the organic industry had estimated sales of more than $1 billion. In 2006, Tom's of Maine was acquired by the Colgate-Palmolive Company. In 2015, Whole Foods had expanded to 365 stores and reported record revenues of almost $15.5 billion.

While natural personal care products have gained "mainstream" consumer acceptance, concerns remain. Many so-called "natural" products are not "natural", and contain significant amounts of synthetic ingredients. Other products include "natural" ingredients at de minimis concentrations, which do not provide health benefits; instead, natural ingredients are added to these products for purposes of "label copy".

As access to the internet became more widespread, consumers took steps to publicly question what is natural, posting blogs and comments calling attention to what can be viewed as deceptive or misleading use of the phrase natural. See, for example, reviews on sites like http://www.naturaltoothpastebrands.com. Additionally, the internet has made do-it-yourself personal product recipes (for skincare, haircare, and oral care) available to consumers. See, for example, http://www.healthyandnaturalworld.com/sage-and-sea-salt-homemade-toothpowder/(¼ cup fresh sage leaves combined with ¾ cup sea salt); see, also, http://www.sproutinghealthyhabits.com/homemade-natural-toothpaste/(2 teaspoons of Dead Sea salt; 3 teaspoons of Himalayan pink salt; 2 teaspoons of ground sage; ⅓ cup of stevia powder; 7-8 Tablespoons Organic Unrefined Cold Pressed Coconut Oil; 8 drops of tea tree essential oil; 40 drops spear[mint] essential oil; 15 drops of pepper[mint] essential oil; 5 teaspoons of Sodium Bentonite Clay)

Access to plethora of information on internet is not, however, without risk. Websites content is not subject to review and can be incomplete, inaccurate, or alarmist. Statements that a particular ingredient is "toxic" are often made without proper context. For example, a 1990 report issued US National Toxicology Program (NTP) reported a higher than expected number of cases of osteosarcoma found "equivocal" evidence of fluoridated drinking water can cause osteosarcoma in male rats. However, exposure to fluoride has been associated with dental and skeletal fluorosis.

Enamel is a quasi-translucent structure which allows the underlying dentin color to show through. Color of teeth (as perceived by others) is determined by the transparency of the enamel, the color tone of the underlying dentin and any imbedded staining contained between the dentin and the enamel surface. It is also associated with the light scattering and absorption properties of the enamel and dentin.

Tooth discoloration (staining) is multifactorial condition influenced by oral hygiene, diet (foods and beverages that are acidic and/or contain tannins and other chromogenic materials), tobacco usage, and aging. Extrinsic stains appear on the pellicle, the layer of adsorbed salivary proteins and other macromolecules on the dental enamel surface. These stains can be reduced, and future staining can be prevented, through brushing, rinsing and flossing.

Deeper "intrinsic" staining is caused by long-term accumulation of chromogens within the enamel. Intrinsic staining is typically addressed through professional bleaching procedures (either in-office or at-home). These procedures can include bleaching trays and strips.

Causal factors of xerostomia include disease (Sjögren's syndrome, HIV/AIDS, and diabetes), medication (more than 400 medicines, including for high blood pressure and depression, can cause the salivary glands to make less saliva), radiation therapy (directly damages salivary glands), chemotherapy (thickens saliva, causing the mouth to feel dry), and nerve damage.

The present invention seeks to meet the long-felt but as yet unmet need for natural and naturally derived oral care products (in particular, dentrifices and mouthwashes) that contain safe and effective amounts of natural ingredients useful in cleaning and maintaining healthy, attractive teeth and gums. Products of the present invention are tailored to address sensitivity, xerostomia, as well as provide visibly whiter teeth and fresher/cleaner breath.

Periodontal disease affects not only oral health. Recent research has identified potential linkage with systemic conditions such as cardiovascular disease, diabetes, adverse pregnancy outcomes, rheumatic arthritis, aspiration pneumonia and Chronic Obstructive Airways Disease. Periodontal disease is also being investigated as a potential etiological factor in colorectal cancer, oral squamous cell carcinoma, pancreatic cancer and breast cancer.

Mechanical plaque control has limited effectiveness in ensuring oral health; it is arduous, repetitive and time-consuming. For this reason, there exists considerable interest in alternative or adjunct approaches to existing mechanical oral hygiene techniques—notably mouthwashes. However, studies report widely varying levels of effectiveness prior art mouthwashes with regard to plaque removal, and reported side-effects include altered taste and discoloration. Prior art mouthwashes that contain chlorhexidine provide excellent short-term plaque control and concomitant improvement in gingival health. However, use of chlorhexidine mouthwashes is limited due to some of its side effects that include tooth staining and taste alterations after longer usage Moreover, chlorhexidine has been shown ex vivo to have a cytotoxic effect on cells. Thus, there is a continued need for new mouthwash formulations for improving plaque control. That need is met by the present invention.

SUMMARY OF THE INVENTION

The present invention is directed to oral care products consisting essentially of a Sea Salt, at least one essential oil, xylitol, and preferably, aloe vera juice and uses of such compositions to whiten teeth, reduce sensitivity of teeth/gums, and reduce xerostomia. In certain preferred embodiments directed to whitening and xerostomia, the compositions also include coconut oil.

DETAILED DESCRIPTION OF THE INVENTION

Sea Salt is a mixture of inorganic salts from sea water or from inland bodies of salt water. Sea Salt may be in the form of a precipitate (on the bottom of a marsh or salt pan or flat) or crystals that float on the surface of the water (known as fleur de sel). One particularly preferred Sea Salt suitable for use in the oral care products of the present invention is Dead Sea Salt is a mixture of natural hygroscopic minerals and micronutrients found in the Dead Sea and is comprised of sodium chloride, magnesium, potassium, and calcium chlorides and bromides. A non-limiting compositional analysis of Dead Sea Salt versus Common Salt is presented in the table below:

|  | Dead Sea Salt (%) | Common Salt (%) |
|---|---|---|
| $H_2O$ | 37.5 | 0.33 |
| $MgCl_2$ | 32.2 | 0.18 |
| KCl | 24.5 | 0.14 |
| NaCl | 5.6 | 99.2 |
| $CaCl_2$ | 6.23 | 0.15 |
| $Br^-$ | 0.35 | 0.052 |
| $Rb^+$ | 0.025 | — |
| $Li^+$ | 1.0 | — |
| $Fe^{3+}$ | 0.00203 | 0.00016 |
| $Al^{3+}$ | 0.00037 | 0.000028 |
| $SO_4^{2-}$ | 0.00916 | 0.0311 |
| $Sr^{2+}$ | 0.00153 | 0.00047 |
| $Mn^{2+}$ | 0.00023 | 0.0038 |

S. Halevy et al., J. Eur. Acad. Dermatol. Venereol., Vol. 9, pp. 237-242 (1997).

Another preferred Sea Salt suitable for use in the oral care products of the present invention is Himalayan Salt, which is harvested from the Punjab Region of Pakistan, and is comprised of sodium chloride (about 95-98%), with about 2 to 3% polyhalite (potassium, calcium, magnesium, sulfur, oxygen, hydrogen), fluoride, iodine, and smaller amounts of other trace minerals.

Xylitol is the pentahydric alcohol that conforms to the formula:

Xylitol is present in oral care products of the invention at a concentration of at least about 7.5%, more preferably at least about 10%, or at a dose of about 0.1 g/brushing or rinsing.

Products of the present invention contain one or more essential oils. As used in the present application, essential oils are a mixture of terpenic hydrocarbons, especially monoterpenes and sesquiterpenes, and oxygenated derivatives such as aldehydes, ketones, epoxides, alcohols, and esters.

*Mentha Viridis* (Spearmint) Leaf Oil is the volatile oil obtained from the leaves of *Mentha viridis*. It consists largely of carvone. The accepted scientific name for *Mentha viridis* is *Mentha spicata*.

*Gaultheria Procumbens* (Wintergreen) Leaf Oil is the volatile oil obtained from the leaves of *Gaultheria procumbens*.

*Mentha Piperita* (Peppermint) Oil is a volatile oil obtained from the whole plant *Mentha piperita*. The accepted scientific name for *Mentha piperita* is *Mentha× piperita*.

*Ocimum Basilicum* (Holy Basil) Oil is a volatile oil obtained from *Ocimum basilicum*.

*Eugenia Caryophyllus* (Clove) Flower Oil is the volatile oil obtained from the flowers of *Eugenia caryophyllus*. It consists chiefly of eugenol. The accepted scientific name for *Eugenia caryophyllus* is *Syzygium aromaticum*.

*Citrus Limon* (Lemon) Peel Oil is the volatile oil obtained from the peel of *Citrus limon*.

*Salvia Officinalis* (Sage) Oil is the essential oil derived from the herbal plant, *Salvia officinalis*.

*Cocos Nucifera* (Coconut) Oil is an oil obtained from the kernel or seed of *Cocos nucifera*.

Other essential oils that may be included in the oral care products of the present invention include *Melaleuca Alternifolia* (Tea Tree) Leaf Oil, the oil distilled from the leaves of the *Melaleuca alternifolia*, and *Zingiber Officinale* (Ginger) Root Oil, which is obtained from the dried rhizomes of *Zingiber officinale*.

Dentifrices and Mouthwashes of the Invention

Certain aspects of the present invention are directed to oral care products—dentrifices and mouthwashes—consisting essentially of a Sea Salt, preferably selected from the group of Dead Sea Salt, and Himalyan Salt (each as defined above), aloe vera extract (juice), at least one essential oil, and xylitol.

Aloe Vera Juice is present in oral care products of the invention at a concentration of at least about 1%, preferably a concentration of at least about 20%, and still more preferably a concentration of at least about 40%.

Dead Sea Salt is present in oral care products of the invention of the invention at a concentration of less than about 3%, preferably a concentration of from about 0.1% to 2%, still more preferably a concentration of from about 0.5% to about 1.5%.

The at least one essential oil in the oral care products of the invention is preferably an aromatic plant in the family Labiatae.

In one set of preferred embodiments the at least one essential oil in the family Labiatae is a plant in the genus *Mentha*, even more preferably *Mentha Piperita* (Peppermint) Oil and *Mentha Viridis* (Spearmint) Leaf Oil.

In yet another preferred embodiment the at least one essential oil is *Gaultheria Procumbens* (Wintergreen) Leaf Oil.

In one even more preferred embodiment, the oral care products of the present invention the at least one essential oil is peppermint and one of wintergreen or spearmint.

In another even more preferred embodiment, the oral care products of the present invention the at least one essential oil is wintergreen and one of peppermint or spearmint.

In a still further even more preferred embodiment, the oral care products of the present invention the at least one essential oil is spearmint and one of peppermint or wintergreen.

In embodiments of the invention in which Wintergreen Oil, it is present preferably at a concentration of up to about 1%, preferably from about 0.1% to about 0.5%.

In embodiments of the invention in which Peppermint Oil, it is preferably at a concentration up to about 0.1%, preferably less than about 0.075%, and more preferably at a concentration of less than about 0.05%.

In embodiments of the invention in which Spearmint Oil is present, it is preferably at a concentration of up to about 4%, preferably up to about 2%, more preferably up to about 1%, and still more preferably less than about 0.5%.

In some preferred toothpaste embodiments, the weight ratio of wintergreen to peppermint is about 10:1.

In other preferred toothpaste embodiments, the weight ratio of spearmint to peppermint is about 3:1.

In still other preferred toothpaste embodiments, the weight ratio of wintergreen to spearmint is about 3:1.

In yet another preferred toothpaste embodiment that contains wintergreen, spearmint and peppermint, the weight ratio of wintergreen to spearmint and peppermint is about 3:1.

In one preferred mouthwash embodiment, the weight ratio of wintergreen to peppermint is from about 6:1 to about 5:1.

In another preferred mouthwash embodiment, the weight ratio of spearmint to peppermint is about 5:3.

In still another preferred mouthwash embodiment, the weight ratio of wintergreen to spearmint is about 4:1.

In a still further preferred mouthwash embodiment that contains wintergreen, spearmint and peppermint, the weight ratio of wintergreen to spearmint and peppermint is about 2:1.

In embodiments of the invention that contain peppermint, the concentration of peppermint is preferably not in excess of about 0.05%, more preferably not in excess of about 0.025%.

Menthol, an alcohol that can be isolated from peppermint or other mint oils, can also be used in oral care products of the present invention.

In another preferred embodiment the at least one essential oil in the family Labiatae is a plant in the genus *Ocimum*.

Preferably, the oral care products of the present invention contain *Ocimum Basilicum* (Basil) Extract and/or *Eugenia Caryophyllus* (Clove) Flower Oil. In especially preferred embodiments, the oral care products of the present invention contain both basil leaf extract and clove flower extract.

In certain preferred embodiments of the invention that contain *Ocimum Basilicum* (Basil) Oil, the basil oil is present at a concentration of up to about 0.5%.

In certain preferred embodiments of the invention that contain *Eugenia Caryophyllus* (Clove) Flower Oil, clove oil is present at a concentration of at least about 0.005%. In other preferred embodiments of the invention, clove oil is present at a concentration of at least about 0.01%. In certain of these preferred embodiments, clove oil is preferably at a concentration of up to about 0.02%.

The oral care products of the present invention may be administered in the form of a dentifrice or mouthwash.

By the term "dentifrice" is meant a preparation for cleansing and polishing the teeth, that may, and preferably does contain one or more therapeutic products. As will be understood by the skilled artisan, a dentifrice (also referred to in the art and in this application as a "toothpaste") may be formulated as a paste, gel or powder.

Dentifrice embodiments of the present invention may include mild abrasives (to remove debris and residual surface stains), humectants (to prevent water loss in the toothpaste), thickening products, also known in the art as binders (to stabilize the toothpaste formula), flavoring products (for taste) and detergents (to create foaming action).

Mild abrasives suitable for use in the toothpaste embodiments of the present invention include calcium carbonate, dehydrated silica gels, hydrated aluminum oxides, magnesium carbonate, phosphate salts and silicates. Silica, also called silicone dioxide, bentonite clay and hydrated silica are minerals.

Toothpastes of the present invention preferably contain is hydrated silica. When present, hydrated silica is preferably incorporated into toothpaste formulations of the invention at a concentration of from about 10% to about 25%.

Humectants that may be, and preferably are, ingredients in toothpastes of the present invention include glycerin, propylene, glycol and sorbitol.

Glycerin, a sugar alcohol that can be synthesized or obtained from natural sources, is an especially preferred humectant used in toothpastes of the invention. When present, toothpastes of the invention contain glycerin at a concentration of from about 2.5% to about 20%, preferably from about 5.0% to about 15%.

Non-limiting examples of thickening products that may be, and preferably are included in toothpaste embodiments of the present invention include gums and colloids, and cellulosics. Preferred colloids are of marine origin, even more preferably seaweed colloids.

Two preferred gums are Xanthan Gum and Biosaccharide Gum-1; both are polysaccharides derived from the fermentation of carbohydrates. Xanthan Gum is derived from glucose or corn syrup. Biosaccharide Gum-1 is derived from sorbitol.

Xanthan Gum may be, and preferably is present in toothpastes of the invention, preferably at a concentration of at least about 0.10.

Carrageenan, a polysaccharide hydrocolloid obtained from edible red seaweeds in the Gigartinaceae or Solieriaceae families, may be, and preferably is, present in toothpastes of the invention. When present, toothpastes of the invention preferably contain carrageenan at a concentration of at least about 0.05%.

Dentrifice compositions of the present invention preferably contain a foaming anionic other than Sodium Lauryl Sulfate, preferably Sodium Methyl Cocoyl Taurate or Sodium Lauroyl Sarcosinate. In certain preferred embodiments, Sodium Methyl Cocoyl Taurate is present in toothpastes of the invention at a concentration of up to about 2%.

Titanium Dioxide may be present in certain toothpastes of the invention; when present, toothpastes of the invention contain titanium dioxide at a concentration of up to about 0.6%.

As discussed below with reference to specific embodiments, the oral care products of the present invention contain one or more therapeutic product(s) that provide(s) one or more of the following oral health and/or cosmetic benefits: (i) inhibition of the formation of dental caries; (ii) inhibition of the formation of gingivitis and plaque; (iii) whitening of teeth surfaces; (iv) reduction in sensitivity, as defined below; (v) reduction in symptoms associated with xerostomia.

Whitening mouthwashes and whitening toothpastes of the invention preferably contain *Cocos Nucifera* (Coconut) Oil and, optionally, but preferably, at least one of *Citrus Limon* (Lemon) Peel Oil and/or *Salvia Officinalis* (Sage) Oil.

In certain preferred embodiments, whitening mouthwashes and whitening toothpastes of the invention preferably contain *Cocos Nucifera* (Coconut) Oil, *Citrus Limon* (Lemon) Peel Oil, and *Salvia Officinalis* (Sage) Oil.

In certain preferred embodiments of the present invention, whitening oral care products (both dentrifices and mouthwashes) contain *Cocos Nucifera* (Coconut) Oil and *Citrus Limon* (Lemon) Peel Oil in a ratio of about 1:1.

In other preferred embodiments of the present invention, whitening dentrifices and whitening mouthwashes contain *Cocos Nucifera* (Coconut) Oil, *Citrus Limon* (Lemon) Peel Oil, and *Salvia Officinalis* (Sage) Oil in a ratio of about 1:1:1.

Preferably, *Cocos Nucifera* (Coconut) Oil and *Citrus Limon* (Lemon) Peel Oil are present in whitening oral care products of the invention at a concentration of at least 0.01%.

In oral care products of the invention formulated for use by individuals having xerostomia, the compositions contain one, preferably two, and still more preferably three of the following ingredients: *Cocos Nucifera* (Coconut) Oil, *Capsicum Frutescens* Fruit Extract, *Vitis Vinifera* (Grape) Seed Oil, and *Sesamum Indicum* (Sesame) Seed Oil.

In one especially preferred embodiment the oral care composition used to reduce xerostomia contains *Cocos Nucifera* (Coconut) Oil, *Capsicum Frutescens* Fruit Extract and one of *Vitis Vinifera* (Grape) Seed Oil or *Sesamum Indicum* (Sesame) Seed Oil.

While oral care products of the present invention are preferably not fluoridated, fluoride may be included certain formulations within the scope of the invention to strengthen tooth enamel and remineralize teeth.

Oral care products of the present invention may also be in the form of a whitening strip with a hydratable adhesive firm—one which hydrates in water or saliva and thereby adheres (sticks) to teeth.

The following formulations are non-limiting examples of embodiments of the dentrifices and mouthwashes within the scope of the invention.

Some toothpastes of the present invention are formulated for use by the general population. These toothpastes for the general population contain the following ingredients at the following concentrations:

Aloe Vera Juice is present in toothpastes formulated for use by the general population at a concentration of at least about 10%, preferably at least about 20%, and most preferably at least about 40%.

Glycerin is present in toothpastes formulated for use by the general population at a concentration of from about 2.5% to about 20%, preferably from about 5.0% to about 15%.

Carrageenan may be, and preferably is, present in toothpastes of the invention, preferably at a concentration of at least about 0.1%.

Xanthan Gum may be, and preferably is present in toothpastes of the invention, preferably at a concentration of at least about 0.10.

Xylitol is present in toothpastes of the present invention at a concentration of at least 10% or at a dose of 0.1 g/brushing.

Titanium Dioxide may be present in certain toothpastes of the invention; when present, titanium dioxide is present at a concentration of up to about 0.5%.

Hydrated Silica is present in toothpastes of the invention, preferably at a concentration of from about 10% to about 20%.

Compositions of the present invention contain a foaming anionic other than Sodium Lauryl Sulfate, preferably Sodium Methyl Cocoyl Taurate or Sodium Lauroyl Sarcosinate. In certain preferred embodiments, Sodium Methyl Cocoyl Taurate is present in toothpastes of the invention at a concentration of up to about 2%.

Dead Sea Salt is present in toothpastes of the invention at a concentration of less than about 3%, preferably from about 0.5% to 2%, most preferably from about 0.75% to about 1.5%.

Holy Basil Oil is present in toothpastes of the invention, preferably at a concentration of up to about 0.05%.

Peppermint Oil is present in toothpastes of the invention at a concentration of less than 1%, preferably less than about 0.075%, more preferably at a concentration of less than about 0.05%, and even more preferably at a concentration of about 0.03%.

Spearmint Oil is present in toothpastes of the invention, preferably at a concentration of up to about 4%, preferably up to about 2%, more preferably up to about 1%, and still more preferably less than about 0.5%.

Wintergreen Oil is present in toothpastes of the invention, preferably at a concentration of up to about 1%, preferably from about 0.25% to about 0.5%.

Clove Oil is present in toothpastes of the invention, preferably at a concentration of up to about 0.05%.

Other toothpastes of the present invention are formulated for whitening teeth. These whitening toothpastes contain the following ingredients at the following concentrations.

Aloe Vera Juice is present in toothpastes formulated for whitening teeth at a concentration of from about 10% to about 90%, preferably from about 20% to about 85%, and most preferably from about 40% to about 70%.

Glycerin is present in toothpastes formulated for whitening teeth at a concentration of from about 5% to about 20%, preferably from about 8% to about 12%, and most preferably from about 10%.

Carrageenan is present in toothpastes formulated for whitening teeth at a concentration of from about 0.05% to about 5%, preferably from about 0.1% to about 0.3%, and most preferably from about 0.15% to about 0.25%.

Xanthan Gum is present in toothpastes formulated for whitening teeth at a concentration of from about 0.1% to about 1.0%, preferably from about 0.4% to about 0.8%, and most preferably from about 0.5% to about 0.7%.

Xylitol is present in toothpastes formulated for whitening teeth at a concentration of from about 5% to about 30%, preferably from about 15% to about 25%, and most preferably from about 17% to about 22%.

Titanium Dioxide is present in toothpastes formulated for whitening teeth at a concentration of from about 0.01% to about 1.0%, preferably from about 0.03% to about 0.07%, and most preferably from about 0.4% to about 0.6%.

Hydrated Silica is present in toothpastes formulated for whitening teeth at a concentration of from about 5% to about 25%, preferably from about 10% to about 20%, and most preferably from about 14% to about 17%.

Sodium Methyl Cocoyl Taurate is present in toothpastes formulated for whitening teeth at a concentration of from about 0.3% to about 2%, preferably from about 0.5% to about 1.5%, and most preferably from about 0.8% to about 1.2%.

Dead Sea Salt is present in toothpastes formulated for whitening teeth at a concentration of from about 0.5% to about 3.0%, preferably from about 0.75% to about 1.75%, and most preferably from about 1.0% to about 1.5%.

Holy Basil Oil is present in toothpastes formulated for whitening teeth at a concentration of from about 0.001% to about 0.05%, preferably from about 0.005% to about 0.03%, and most preferably from about 0.02% to about 0.035%.

Peppermint Oil is present in toothpastes formulated for whitening teeth at a concentration of from about 0.001% to about 0.07%, preferably from about 0.005% to about 0.06%, and most preferably from about 0.01% to about 0.03%.

Spearmint Oil is present in toothpastes formulated for whitening teeth at a concentration of from about 0.01% to about 2%, preferably from about 0.05% to about 1.5%, and most preferably from about 0.09% to about 1.2%.

Wintergreen Oil is present in toothpastes formulated for whitening teeth at a concentration of from about 0.05% to about 1%, preferably from about 0.1% to about 0.5%, and most preferably from about 0.2% to about 0.4%.

Clove Oil is present in toothpastes formulated for whitening teeth at a concentration of from about 0.001% to about 0.05%, preferably from about 0.005% to about 0.04, and most preferably from about 0.01% to about 0.03%.

Coconut Oil is present in toothpastes formulated for whitening teeth at a concentration of from about 0.001% to about 5%, preferably from about 0.005% to about 1%, and most preferably from about 0.09% to about 0.9%.

Lemon Peel Oil is present in toothpastes formulated for whitening teeth at a concentration of from about 0.001% to about 5%, preferably from about 0.005% to about 1%, and most preferably from about 0.09% to about 0.9%.

Sage Oil is present in toothpastes formulated for whitening teeth at a concentration of from about 0.001% to about 5%, preferably from about 0.005% to about 1%, and most preferably from about 0.09% to about 0.9%.

Certain toothpastes of the present invention are formulated for use by individuals having sensitive teeth and/or gums. These sensitivity toothpastes contain the following ingredients at the following concentrations.

Aloe Vera Juice is present in toothpastes formulated for use by individuals having sensitive teeth and/or gums at a concentration of from about 10% to about 90%, preferably from about 20% to about 85%, and most preferably from about 40% to about 70%.

Glycerin is present in toothpastes formulated for use by individuals having sensitive teeth and/or gums at a concentration of from about 5% to about 20%, preferably from about 8% to about 12%, and most preferably from about 0.1.

Carrageenan is present in toothpastes formulated for use by individuals having sensitive teeth and/or gums at a concentration of from about 0.05% to about 5%, preferably from about 0.1% to about 0.3%, and most preferably from about 0.15% to about 0.25%.

Xanthan Gum is present in toothpastes formulated for use by individuals having sensitive teeth and/or gums at a concentration of from about 0.1% to about 1.0%, preferably from about 0.4% to about 0.8%, and most preferably from about 0.5% to about 0.7%.

Xylitol is present in toothpastes formulated for use by individuals having sensitive teeth and/or gums at a concentration of from about 5% to about 30%, preferably from about 15% to about 25%, and most preferably from about 17% to about 22%.

Titanium Dioxide is present in toothpastes formulated for use by individuals having sensitive teeth and/or gums at a concentration of from about 0.01% to about 1.0%, preferably from about 0.03% to about 0.07%, and most preferably from about 0.4% to about 0.6%.

Hydrated Silica is present in toothpastes formulated for use by individuals having sensitive teeth and/or gums at a concentration of from about 5% to about 25%, preferably from about 10% to about 20%, and most preferably from about 15% to about 17%.

Sodium Methyl Cocoyl Taurate is present in toothpastes formulated for use by individuals having sensitive teeth and/or gums at a concentration of from about 0.3% to about 2%, preferably from about 0.5% to about 1.5%, and most preferably from about 0.8% to about 1.2%.

Dead Sea Salt is present in toothpastes formulated for use by individuals having sensitive teeth and/or gums at a concentration of from about 0.5% to about 3.0%, preferably from about 0.7% to about 1.75%, and most preferably from about 1.0% to about 1.5%.

Holy Basil Oil is present in toothpastes formulated for use by individuals having sensitive teeth and/or gums at a concentration of from about 0.001% to about 0.05%, preferably from about 0.005% to about 0.03%, and most preferably from about 0.015% to about 0.03%.

Peppermint Oil is present in toothpastes formulated for use by individuals having sensitive teeth and/or gums at a concentration of from about 0.001% to about 0.07%, preferably from about 0.005% to about 0.06%, and most preferably from about 0.01% to about 0.03%.

Spearmint Oil is present in toothpastes formulated for use by individuals having sensitive teeth and/or gums at a concentration of from about 0.01% to about 2%, preferably from about 0.05% to about 1.5%, and most preferably from about 0.05% to about 1.0%.

Wintergreen Oil is present in toothpastes formulated for use by individuals having sensitive teeth and/or gums at a concentration of from about 0.05% to about 1%, preferably from about 0.1% to about 0.5%, and most preferably from about 0.15% to about 0.3%.

Clove Oil is present in toothpastes formulated for use by individuals having sensitive teeth and/or gums at a concentration of from about 0.001% to about 0.05%, preferably from about 0.005% to about 0.04%, and most preferably from about 0.01% to about 0.03%.

Still other toothpastes of the present invention formulated for use by individuals having xerostomia. These xerostomia toothpastes contain the following ingredients at the following concentrations.

Aloe Vera Juice is present in toothpastes formulated for use by individuals having xerostomia at a concentration of from about 10% to about 90%, preferably from about 20% to about 85%, and most preferably from about 40% to about 70%.

Glycerin is present in toothpastes formulated for use by individuals having xerostomia at a concentration of from about 5% to about 20%, preferably from about 8% to about 12%, and most preferably from about 0.1.

Carrageenan is present in toothpastes formulated for use by individuals having xerostomia at a concentration of from about 0.05% to about 5%, preferably from about 0.1% to about 0.3%, and most preferably from about 0.15% to about 0.25%.

Xanthan Gum is present in toothpastes formulated for use by individuals having xerostomia at a concentration of from about 0.1% to about 1.0%, preferably from about 0.4% to about 0.8%, and most preferably from about 0.5% to about 0.7%.

Xylitol is present in toothpastes formulated for use by individuals having xerostomia at a concentration of from about 10% to about 30%, preferably from about 15% to about 25%, and most preferably from about 17% to about 22%.

Titanium Dioxide is present in toothpastes formulated for use by individuals having xerostomia at a concentration of from about 0.01% to about 1.0%, preferably from about 0.03% to about 0.07%, and most preferably from about 0.4% to about 0.6%.

Hydrated Silica is present in toothpastes formulated for use by individuals having xerostomia at a concentration of from about 5% to about 25%, preferably from about 10% to about 20%, and most preferably from about 15% to about 17%.

Sodium Methyl Cocoyl Taurate is present in toothpastes formulated for use by individuals having xerostomia at a concentration of from about 0.3% to about 2%, preferably from about 0.5% to about 1.5%, and most preferably from about 0.8% to about 1.2%.

Dead Sea Salt is present in toothpastes formulated for use by individuals having xerostomia at a concentration of from about 0.5% to about 3.0%, preferably from about 0.7% to about 1.75%, and most preferably from about 1.0% to about 1.5%.

Holy Basil Oil is present in toothpastes formulated for use by individuals having xerostomia at a concentration of from about 0.001% to about about 0.05% to about 1.0%.

Wintergreen Oil is present in toothpastes formulated for use by individuals having xerostomia at a concentration of from about 0.05% to about 1%, preferably from about 0.1% to about 0.5%, and most preferably from about 0.15% to about 0.3%.

Clove Oil is present in toothpastes formulated for use by individuals having xerostomia at a concentration of from about 0.001% to about 0.05%, preferably from about 0.005% to about 0.04%, and most preferably from about 0.01% to about 0.03%.

Coconut Oil is present in toothpastes formulated for use by individuals having xerostomia at a concentration of from about 0.001% to about 5%, preferably from about 0.005% to about 1%, and most preferably from about 0.09% to about 0.9%.

Grapeseed Oil is present in toothpastes formulated for use by individuals having xerostomia at a concentration of from about 0.01% to about 1%, preferably from about 0.03% to about 0.5%, and most preferably from about 0.07% to about 0.4%.

Cayenne Pepper Oil is present in toothpastes formulated for use by individuals having xerostomia at a concentration of from about 0.01% to about 1.0%, preferably from about 0.02% to about 0.3%, and most preferably from about 0.03% to about 0.2%.

Some mouthwashes of the present invention are formulated for use by the general population. These mouthwashes for the general population contain the following ingredients at the following concentrations.

Aloe Vera Juice is present in mouthwashes formulated for use by the general population at a concentration of from about 10% to about 90%, preferably from about 20% to about 85%, and most preferably from about 50% to about 70%.

Xylitol is present in mouthwashes formulated for use by the general population at a concentration of from about 5% to about 30%, preferably from about 7% to about 15%, and most preferably from about 8% to about 12%.

Dead Sea Salt is present in mouthwashes formulated for use by the general population at a concentration of from about 0.5% to about 5%, preferably from about 0.75% to about 3%, and most preferably from about 1% to about 2%.

Tulsi Holy Basil is present in mouthwashes formulated for use by the general population at a concentration of from about 0.005% to about 0.5%, preferably from about 0.01% to about 0.2%, and most preferably from about 0.02% to about 0.1%.

Peppermint is present in mouthwashes formulated for use by the general population at a concentration of from about 0.005% to about 0.12%, preferably from about 0.01% to about 0.1%, and most preferably from about 0.02% to about 0.09%.

Spearmint is present in mouthwashes formulated for use by the general population at a concentration of from about 0.01% to about 1%, preferably from about 0.02% to about 0.17%, and most preferably from about 0.05% to about 0.15%.

Wintergreen is present in mouthwashes formulated for use by the general population at a concentration of from about 0.03% to about 1%, preferably from about 0.05% to about 0.5%, and most preferably from about 0.1% to about 0.45%.

Clove is present in mouthwashes formulated for use by the general population at a concentration of from about 0.005% to about 0.075%, preferably from about 0.01% to about 0.04%, and most preferably from about 0.01% to about 0.03%.

Other mouthwashes of the present invention are formulated for whitening. These whitening mouthwashes contain the following ingredients at the following concentrations.

Aloe Vera Juice is present in mouthwashes formulated for whitening teeth at a concentration of from about 10% to about 90%, preferably from about 20% to about 85%, and most preferably from about 50% to about 70%.

Xylitol is present in mouthwashes formulated for whitening teeth at a concentration of from about 5% to about 30%, preferably from about 7% to about 15%, and most preferably from about 8% to about 12%.

Dead Sea Salt is present in mouthwashes formulated for whitening teeth at a concentration of from about 0.5% to about 5%, preferably from about 0.75% to about 3%, and most preferably from about 1% to about 2%.

Tulsi Holy Basil is present in mouthwashes formulated for whitening teeth at a concentration of from about 0.005% to about 0.5%, preferably from about 0.01% to about 0.2%, and most preferably from about 0.02% to about 0.1%.

Peppermint is present in mouthwashes formulated for whitening teeth at a concentration of from about 0.005% to about 0.12%, preferably from about 0.01% to about 0.1%, and most preferably from about 0.02% to about 0.09%.

Spearmint is present in mouthwashes formulated for whitening teeth at a concentration of from about 0.01% to about 1%, preferably from about 0.02% to about 0.17%, and most preferably from about 0.05% to about 0.15%.

Wintergreen is present in mouthwashes formulated for whitening teeth at a concentration of from about 0.03% to about 1%, preferably from about 0.05% to about 0.5%, and most preferably from about 0.1% to about 0.45%.

Clove is present in mouthwashes formulated for whitening teeth at a concentration of from about 0.005% to about 0.075%, preferably from about 0.01% to about 0.04%, and most preferably from about 0.01% to about 0.03%.

Coconut Oil is present in mouthwashes formulated for whitening teeth at a concentration of from about 0.001% to about 5%, preferably from about 0.1% to about 0.7%, and most preferably from about 0.15% to about 0.6%.

Lemon Peel Oil is present in mouthwashes formulated for whitening teeth at a concentration of from about 0.001% to about 5%, preferably from about 0.1% to about 0.7%, and most preferably from about 0.15% to about 0.6%.

Sage Oil is present in mouthwashes formulated for whitening teeth at a concentration of from about 0.001% to about 0.09%, preferably from about 0.005% to about 0.05%, and most preferably from about 0.01% to about 0.03%.

Certain mouthwashes of the present invention are formulated for use by individuals having sensitive teeth and/or gums. These sensitivity mouthwashes contain the following ingredients at the following concentrations.

Aloe Vera Juice is present in mouthwashes formulated for use by individuals having sensitive teeth and/or gums at a concentration of from about 10% to about 90%, preferably from about 20% to about 85%, and most preferably from about 50% to about 70%.

Xylitol is present in mouthwashes formulated for use by individuals having sensitive teeth and/or gums at a concentration of from about 5% to about 30%, preferably from about 7% to about 15%, and most preferably from about 8% to about 12%.

Dead Sea Salt is present in mouthwashes formulated for use by individuals having sensitive teeth and/or gums at a concentration of from about 0.5% to about 5%, preferably from about 0.75% to about 3%, and most preferably from about 1% to about 2%.

Tulsi Holy Basil is present in mouthwashes formulated for use by individuals having sensitive teeth and/or gums at a concentration of from about 0.005% to about 0.5%, preferably from about 0.01% to about 0.2%, and most preferably from about 0.02% to about 0.1%.

Peppermint is present in mouthwashes formulated for use by individuals having sensitive teeth and/or gums at a concentration of from about 0.005% to about 0.12%, preferably from about 0.01% to about 0.1%, and most preferably from about 0.02% to about 0.09%.

Spearmint is present in mouthwashes formulated for use by individuals having sensitive teeth and/or gums at a concentration of from about 0.01% to about 1%, preferably from about 0.02% to about 0.17%, and most preferably from about 0.05% to about 0.15%.

Wintergreen is present in mouthwashes formulated for use by individuals having sensitive teeth and/or gums at a concentration of from about 0.03% to about 1%, preferably from about 0.05% to about 0.5%, and most preferably from about 0.1% to about 0.45%.

Clove is present in mouthwashes formulated for use by individuals having sensitive teeth and/or gums at a concentration of from about 0.005% to about 0.075%, preferably from about 0.01% to about 0.04%, and most preferably from about 0.01% to about 0.03%.

Still other mouthwashes of the present invention are formulated for use by individuals having xerostomia. These xerostomia mouthwashes contain the following ingredients at the following concentrations.

Aloe Vera Juice is present in mouthwashes formulated for use by individuals having xerostomia at a concentration of from about 10% to about 90%, preferably from about 20% to about 85%, and most preferably from about 50% to about 70%.

Xylitol is present in mouthwashes formulated for use by individuals having xerostomia at a concentration of from about 5% to about 30%, preferably from about 7% to about 15%, and most preferably from about 8% to about 12%.

Dead Sea Salt is present in mouthwashes formulated for use by individuals having xerostomia at a concentration of from about 0.1% to about 5%, preferably from about 0.5% to about 3%, and most preferably from about 0.6% to about 2%.

Tulsi Holy Basil is present in mouthwashes formulated for use by individuals having xerostomia at a concentration of from about 0.005% to about 0.5%, preferably from about 0.01% to about 0.2%, and most preferably from about 0.02% to about 0.1%.

Peppermint is present in mouthwashes formulated for use by individuals having xerostomia at a concentration of from about 0.005% to about 0.12%, preferably from about 0.01% to about 0.1%, and most preferably from about 0.02% to about 0.09%.

Spearmint is present in mouthwashes formulated for use by individuals having xerostomia at a concentration of from about 0.01% to about 1%, preferably from about 0.02% to about 0.17%, and most preferably from about 0.05% to about 0.15%.

Wintergreen is present in mouthwashes formulated for use by individuals having xerostomia at a concentration of from about 0.03% to about 1%, preferably from about 0.05% to about 0.5%, and most preferably from about 0.1% to about 0.45%.

Clove is present in mouthwashes formulated for use by individuals having xerostomia at a concentration of from about 0.005% to about 0.075%, preferably from about 0.01% to about 0.04%, and most preferably from about 0.01% to about 0.03%.

Coconut Oil is present in mouthwashes formulated for use by individuals having xerostomia at a concentration of from about 0.001% to about 5%, preferably from about 0.1% to about 0.7%, and most preferably from about 0.15% to about 0.6%.

Grape seed oil is present in mouthwashes formulated for use by individuals having xerostomia at a concentration of from about 0.01% to about 1%, preferably from about 0.03% to about 0.5%, and most preferably from about 0.07% to about 0.3%.

Cayenne Pepper Extract is present in mouthwashes formulated for use by individuals having xerostomia at a concentration of from about 0.01% to about 1.0%, preferably from about 0.02% to about 0.3%, and most preferably from about 0.03% to about 0.15%.

Toothpastes and mouthwashes of the present invention may also, optionally, in place of wintergreen, peppermint and/or spearmint, include flavorants and/or taste masking products known in the art materials. The flavorants may be of natural or synthetic origin. Non-limiting examples of such flavorants include, but are not limited to fruit flavors such as cherry, strawberry, lemon, lime, orange, watermelon, or a mixture of fruit flavors (sometimes known as tutti frutti).

Whitening Strip of the Invention

Whitening Strips of the Invention ("Test Strips") are comprised of: (i) a strip of flexible material that is (a) safe for contact with the structures of the oral cavity of humans (i.e., non-toxic, non-corrosive, and non-irritating), (b) conformable to a plurality of adjacent teeth surfaces and to interstitial spaces between teeth, without permanent deformation thereof and (ii) and a Whitening Composition, preferably a gel, applied to the strip. The strip (with applied whitening composition) is removably attached to a release liner.

The Strip

The strip component may be a single layer of material or a laminate, or a plurality or layers of materials or laminates, a heterogeneous mixture of ingredients, separate stripes or spots or other patterns of ingredients, or a combination of laminates, layers, stripes, and/or spots. The Whitening Composition of the Invention (described below) is applied to a first side of the strip facing a release liner; this side is applied to the teeth surface after the release liner is removed.

The one or more materials/laminates and other components/ingredients (i) meet the flexural rigidity characteristics described below and (ii) is/are compatible with "Active Ingredients" as defined below with reference to the Whitening Composition of the Invention.

By the term "compatible" is meant the material does not react with, or cause the degradation or loss of desired function, by the active ingredients.

The strip may be constructed of polymers, natural and synthetic woven materials, non-woven materials, foil, paper, rubber, and combinations thereof.

In certain preferred embodiments, the material(s) used to construct the strip is/are polymers that are substantially water impermeable as well as polymers or gelling products that are hydratable.

Suitable polymers include, but are not limited to, polyethylene, ethylvinylacetate, ethylvinyl alcohol, polyethylene, polyesters (such as Mylar®, manufactured by DuPont), fluoroplastics (such as Teflon®, manufactured by DuPont), and combinations thereof.

In place of, or in addition to the above listed materials, the strip may be constructed from one or more gelling products known in the art. Suitable gelling products are generally recognized to be safe for oral use, do not readily dissolve in saliva, and do not react with, or inactivate, the active ingredients in the whitening composition. Non-limiting examples of gelling products include: carboxypolymethylene, carboxymethyl cellulose, carboxypropyl cellulose, poloxamer, carrageenan, Veegum, carboxyvinyl polymers, and natural gums such as gum karaya, xanthan gum, Guar gum, gum arabic, gum tragacanth, and mixtures thereof.

One preferred gelling product is carboxypolymethylene, available from B. F. Goodrich Company under the tradename "Carbopol". Particularly preferred Carbopols include Carbopol 934, 940, 941, 956 and mixtures thereof. Particularly preferred is Carbopol 956.

Another preferred gelling/thickening product is polyvinylpyrrolidone. In certain embodiments polyvinylpyrrolidone is of a molecular weight in a range of 1,000,000 to 1,500,000. In certain embodiments, polyvinylpyrrolidone has molecular weight of about 50,000 to about 300,000.

Additional gelling products that impart adhesivity between the strip and the surfaces of the teeth to be treated (i.e., whitened) and are suitable for use in the whitening compositions of the present invention include celluloses (hydroxy ethyl or propyl cellulose, ethyl cellulose) and Polyox® water-soluble resins available from Dow Corning (Midland, Mich.).

Polyox® resins are nonionic, high molecular weight water-soluble poly (ethylene oxide) polymers with molecular weights ranging from 100,000 to about 8,000,000.

Gantrez® copolymers—monoalkyl esters of poly (methyl vinyl ether/maleic acid) with varying ester groups—available from Ashland are also suitable for to thicken the whitening compositions and promote adhesion between the strip and teeth surfaces.

In embodiments of the present invention in which the whitening composition is in the form of a gel, one (or more) of the above listed gelling products is/are preferably from about 0.1% to about 15%, preferably from about 1% to about 10%, more preferably from about 2% to about 8%, and most preferably from about 4% to about 7%, by weight.

In certain embodiments, the strip is less than about 2 mm thick, preferably less than about 1 mm thick, and more preferably less than about 0.5 mm thick, and even more preferably less than about 0.1 mm thick.

Preferably, the strip is configured in a shape that has rounded corners, by which is meant not having any sharp angles or points.

The size (length and width) of the strip of the invention will vary based upon one or more factors, including the number of teeth to be treated (i.e., whitened), the size of the teeth, and personal preference of the wearer.

Preferably, the strip is of a length that covers at least the front 6-10 teeth of the upper or lower rows of teeth that are visible when the wearer is smiling. Optionally, the strip covers the entire upper and/or lower rows of teeth.

In certain embodiments, the length of the strip is from about 2 cm to about 12 cm, preferably from about 4 cm to about 9 cm.

The width of the strip of material will vary depending on whether the strip is intended to cover the front surface of the teeth, or wrap around the teeth and cover both surfaces of the teeth.

In certain embodiments, the width of the strip is from about 0.5 cm to about 4 cm, preferably from about 1 to about 2 cm.

The flexural stiffness of the strip is determined by strip thickness, strip width, and material modulus of elasticity. One method for measuring flexural stiffness of a polymeric strip is ASTM D2923-95, which employs a strain gauge wired to a microammeter. In accordance with this method, the rigidity of the strip is read directly from the microammeter and expressed as grams per centimeter of strip width. A non-limiting, but preferred, instrument for measuring flexural stiffness is Handle-O-Meter®, available from Thwing-Albert Instrument Co. of Philadelphia, Pa.

In certain embodiments of the present invention, the strip has a flexural stiffness of less than about 5 grams/cm, preferably a flexural stiffness less than about 4 grams/cm, more preferably less than about 3 grams/cm, and most preferably from about 0.1 grams/cm to about 1 grams/cm.

In certain embodiments, the flexural stiffness of the strip is substantially constant and does not significantly change during normal use. For example, in these embodiments, the strip does not need to be hydrated for the strip to achieve flexural stiffness in the above-specified ranges.

Low flexural stiffness (in the above-specified ranges) is an important property of the strip, which allows the strip to drape over, and conform to, the contoured surfaces of teeth of the wearer's mouth, including gaps between adjacent teeth. By designing strips to have a flexural stiffness within the above-specified ranges, there are minimal residual forces within the strip that would cause it to return to an original (i.e.) starting configuration which is substantially flat.

Additionally, the flexibility (low flexural stiffness) of the strip enables the strip to contact soft tissue over an extended period of time without physical irritation.

The time required for the active ingredients to be deliver to and act upon the teeth surface, and thereby provide a desired clinical outcome—whitening and/or decreased sensitivity—can range from several minutes to several hours. Accordingly, the second side of the strip (not facing the release liner) is designed to serve as a protective barrier to substantially prevent the whitening composition from coming into contact with saliva as well as the wearer's lips, tongue, and other soft tissue surrounding the teeth (e.g., papilla, marginal gingiva, gingival sulcus, inter dental gingiva, gingival gum structure on lingual and buccal surfaces up to and including muco-gingival junction and the pallet).

The strip may be, and in certain embodiments is, coated with a uniform mixture of Dead Sea Salt, Coconut Oil and Lemon Oil.

The strip may, in certain embodiments, be configured to have shallow recesses to create reservoirs (depots) for the whitening composition of the Invention and/or different oral care products. These recesses may be filled, for example, with: Dead Sea Salt and/or Coconut Oil; a peroxide (e.g., hydrogen peroxide or carbamide peroxide); a combination of one or both of Dead Sea Salt and/or Coconut Oil and a peroxide (for example, Dead Sea Salt and a peroxide; Coconut Oil and a peroxide; Dead Sea Salt, Coconut Oil and a peroxide).

The Release Liner

The release liner may be formed from any material which exhibits less affinity for the whitening composition than the whitening composition exhibits for (a) itself and (b) for the strip. The release liner preferably comprises a rigid sheet of material such as polyethylene, paper, polyester, or other material which is then coated with a non-stick type material. The release liner material may be coated with wax, silicone, polyester such as Teflon®, fluoropolymers, or other non-stick type materials. The release liner material may crack when the strip is flexed.

The release liner may be cut to substantially the same size and shape as the strip or the release liner may be cut larger than the strip to provide a means for separating the release liner from the strip.

The release liner may have a tab, or be scored, to facilitate separation from the strip. Alternatively, the release liner may be two overlapping pieces in a bandage-type design.

The Whitening Composition

The Whitening Composition used in whitening strips is comprised of one or a combination of Active Ingredients, preferably Sea Salt (as defined above), even more preferably Dead Sea Salt, and still more preferably Dead Sea Salt in further combination with one, preferably two, and still more preferably three essential oils selected from the group of *Cocos Nucifera* (Coconut) Oil, *Citrus Limon* (Lemon) Peel Oil, and *Salvia Officinalis* (Sage) Oil.

The Whitening Composition is preferably formulated as a Whitening Gel that is formulated to provide adhesive attachment sufficient to hold the strip in place for a desired period of time to allow the active ingredient(s) to be delivered to, and act on, the teeth surface, and thereby provide a desired clinical outcome—whitening.

In preferred embodiments, the Whitening Composition(s) is homogeneous, and is preferably coated onto the strip in a uniform manner.

In alternate embodiments, more than one Whitening Composition(s) may be coated onto the strip in a series of separate stripes or spots or other patterns of ingredients.

The Whitening Composition(s) can be in the form of a viscous liquid, paste, gel, solution, or other suitable form that provide adhesion as described below.

The viscosity and tackiness of the Whitening Composition(s) are such that the strip remains adhesively attached to a plurality of adjacent teeth for the desired contact time (preferably from about 20 minutes to about 60 minutes) without substantial slippage under the potential friction from the lips, tongue, and other soft tissue rubbing against the strip (e.g., during mouth movements associated with talking, drinking, etc.

The viscosity and tackiness of the Whitening Composition(s) are such that the strip can be easily removed by the wearer without the use of an instrument, a chemical solvent, or undue friction. Instead, the wearer is able to apply a peel force to remove the strip off the teeth using a finger or fingernail.

In preferred embodiments, the peel force required to remove the strip is from about 1 gram to about 50 grams for a strip that is 1.5 cm in width. Even more preferably, for a strip that is 1.5 cm in width, the peel force is from about 5 grams to about 40 grams, and more preferably from about 10 grams to about 30 grams.

Preferably, the Whitening Composition(s) is in the form of a gel, and has a viscosity of from about 200 to about 1,000,000 at low shear rates (less than one 1/seconds). More preferably, the viscosity is from about 100,000 to about 800,000 cps, and even more preferably the viscosity is from about 400,000 to about 600,000 cps.

The Whitening Composition(s) applied to the strip of the present invention preferably includes a Sea Salt, a mixture of inorganic salts from sea water or from inland bodies of salt water. Sea Salt may be in the form of a precipitate (on the bottom of a marsh or salt pan or flat) or crystals that float on the surface of the water (known as fleur de sel).

The Whitening Composition applied to the strip of the present invention preferably includes one, even more preferably two, and still more preferably all three essential oils selected from the group of *Cocos Nucifera* (Coconut) Oil, *Citrus Limon* (Lemon) Peel Oil, and *Salvia Officinalis* (Sage) Oil In addition to Sea Salt, one or more of the following Active Ingredients are also suitable for inclusion in the strips of the present invention for purposes of whitening the surface of teeth (i.e., bleaching or stain removal): peroxides, metal chlorites, perborates, percarbonates, peroxyacids, and combinations thereof.

The peroxide compound should provide an amount of hydrogen peroxide equivalent of from about 0.1% to about 20%, preferably from about 0.5% to about 10%, and most preferably from about 1% to about 7%, by weight of the substance. Preferred peroxide compounds include hydrogen peroxide, calcium peroxide, carbamide peroxide, and mixtures thereof.

A particularly preferred peroxide is carbamide peroxide. To deliver the desired amount of hydrogen peroxide equivalent carbamide peroxide would be included in the whitening composition in an amount of from about 0.1% to about 30% and preferably from about 3% to about 20% on a weight/weight basis.

Preferred metal chlorites include calcium chlorite, barium chlorite, magnesium chlorite, lithium chlorite, sodium chlorite, and potassium chlorite.

Other Active Ingredients suitable for inclusion in the strips of the present invention for purposes of whitening the surface of teeth include hypochlorite and chlorine dioxide.

The Whitening Compositions that are a component of the delivery system of the present invention may, and preferably do, contain one or more pH adjusting products, non-limiting examples of which include sodium bicarbonate, sodium phosphate, sodium hydroxide, ammonium hydroxide, sodium stannate, triethanolamine, citric acid, hydrochloric acid, sodium citrate, and combinations thereof. pH adjusting products are added in sufficient amounts so as to adjust the pH of the gel composition to about 4.5 to about 11, preferably from about 5 to about 8.5, and more preferably from about 5.5 to about 7. pH adjusting products are generally present in an amount of from about 0.01% to about 15% and preferably from about 0.05% to about 5%, on a weight/weight basis.

The Whitening Compositions of the present invention preferably include one or more humectants. Suitable humectants include glycerin, sorbitol, polyethylene glycol, propylene glycol, and other edible polyhydric alcohols. Humectants are generally present in an amount of from about 10% to about 95%, preferably from about 20% to about 80%, and more preferably from about 50% to about 70%, on a weight/weight basis.

Additional ingredients that may be included in the Whitening Compositions of the present invention include, but are not limited to, flavoring products, sweetening products, xylitol, opacifiers, coloring products, and chelators, such as ethylenediaminetetraacetic acid.

The whitening strip may, in other embodiments, be in the form of a hydratable adhesive film—one which hydrates in water or saliva and thereby adheres (sticks) to teeth.

Whitening Strips of the present invention include Dead Sea Salt in combination with one, preferably two, and still more preferably three essential oils selected from the group of *Cocos Nucifera* (Coconut) Oil, *Citrus Limon* (Lemon) Peel Oil, and *Salvia Officinalis* (Sage) Oil.

In one preferred embodiment, whitening strips of the present invention include Dead Sea Salt, Coconut Oil, Lemon Oil and Sage Oil, each a concentration of up to about 10.0%, preferably each a concentration of up to about 5.0%, and even more preferably at a concentration of at least about 3.0%.

Each of these ingredients is preferably present at a concentration of up to about 800 grams, and more preferably up to about 400 grams.

In one especially preferred embodiment, whitening strips of the present invention include Dead Sea Salt, Coconut Oil, Lemon Oil and Sage Oil in a ratio of about 1:1:1:1.

In one especially preferred embodiment, the whitening strips of the present invention preferably include a hydratable adhesive matrix comprised of glycerol, carbomer and a cellulose, preferably carboxymethylcellulose.

EXAMPLES

The examples above and following illustrate the practice of the present invention in some of its embodiments, the examples should not be construed as limiting the scope of the invention. Other embodiments will be apparent to one skilled in the art from consideration of the specification and examples. It is intended that the specification, including the examples, is considered exemplary only without limiting the scope and spirit of the invention.

Some of the examples illustrate preferred embodiments of the invention. Variations of these preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, unless otherwise indicated herein or otherwise clearly contradicted by context, the inventions include all modifications and equivalents of the subject matter disclosed and recited in the claims appended hereto as permitted by applicable law.

Whitening Mouthwash of Invention ("Test Mouthwash")

Preferred whitening mouthwashes of the present invention consist essentially of a Sea Salt, preferably selected from the group of Dead Sea Salt, and Himalyan Salt (each as defined above), aloe vera extract (juice), at least one essential oil, and, optionally, but preferably, xylitol.

Sea Salt, and in particular Dead Sea Salt, which is an integral component of the inventive whitening mouthwashes is described in Section 1.c above. Dead Sea Salt is preferably present at a concentration of less than about 3%, preferably a concentration of from about 0.1% to 2%, still more preferably a concentration of from about 0.5% to about 1.5%.

Aloe Vera Juice is present in the whitening mouthwashes of the invention at a concentration of at least about 1%, preferably a concentration of at least about 20%, and still more preferably a concentration of at least about 40%.

The at least one essential oil in the oral care products of the invention is preferably an aromatic plant in the family Labiatae.

In one set of preferred embodiments the at least one essential oil in the family Labiatae is a plant in the genus *Mentha*, even more preferably *Mentha Piperita* (Peppermint) Oil and *Mentha Viridis* (Spearmint) Leaf Oil.

In yet another preferred embodiment the at least one essential oil is *Gaultheria Procumbens* (Wintergreen) Leaf Oil.

In one even more preferred embodiment, the oral care products of the present invention the at least one essential oil is peppermint and one of wintergreen or spearmint.

In another even more preferred embodiment, the oral care products of the present invention the at least one essential oil is wintergreen and one of peppermint or spearmint.

In a still further even more preferred embodiment, the oral care products of the present invention the at least one essential oil is spearmint and one of peppermint or wintergreen.

In embodiments of the invention in which Wintergreen Oil, it is present preferably at a concentration of up to about 1%, preferably from about 0.1% to about 0.5%.

In embodiments of the invention in which Peppermint Oil, it is preferably at a concentration up to about 0.1%, preferably less than about 0.075%, and more preferably at a concentration of less than about 0.05%.

In embodiments of the invention in which Spearmint Oil is present, it is preferably at a concentration of up to about 4%, preferably up to about 2%, more preferably up to about 1%, and still more preferably less than about 0.5%.

Whitening mouthwashes of the invention preferably contain *Cocos Nucifera* (Coconut) Oil and, optionally, but preferably, at least one of *Citrus Limon* (Lemon) Peel Oil and/or *Salvia Officinalis* (Sage) Oil.

In certain preferred embodiments, whitening mouthwashes of the invention preferably contain *Cocos Nucifera* (Coconut) Oil, *Citrus Limon* (Lemon) Peel Oil, and *Salvia Officinalis* (Sage) Oil.

In certain preferred embodiments of the present invention, whitening mouthwashes contain *Cocos Nucifera* (Coconut) Oil and *Citrus Limon* (Lemon) Peel Oil in a ratio of about 1:1.

In other preferred embodiments of the present invention, whitening mouthwashes of the invention contain *Cocos Nucifera* (Coconut) Oil, *Citrus Limon* (Lemon) Peel Oil, and *Salvia Officinalis* (Sage) Oil in a ratio of about 1:1:1.

Preferably, *Cocos Nucifera* (Coconut) Oil and *Citrus Limon* (Lemon) Peel Oil are present in whitening mouthwashes of the invention at a concentration of at least 0.01%.

Whitening is measured in terms of changes in L* and b* values, based on the CIE 1976 (L*a*b*) system, where "L*" value represents comparative lightness/darkness (lower L* being indicative of darker), and "a*" and "b*" values are chromaticity coordinates (red-green and blue-yellow, respectively). Negative b* scores are indicative of blue color/hue; positive b* values indicate a yellow color/hue. See, A. R. Robertson, "The CIE 1976 color-difference formulae," Color Res. Appl. Vol. 2, pp. 7-11 (1977).

The efficacy of mouthwashes of the Invention ("Test Mouthwash") in brightening/whitening stained dental enamel was evaluated at specific exposure durations, and compared to a commercial whitening mouthwash, Crest® 3D Whitening Mouthwash ("Prior Art Mouthwash"). As detailed below, similar (no statistical difference, $p>0.05$) outcomes/results were observed (in terms of desired color change) based on treatment using the Test and Prior Art Mouthwashes.

Whitening Strips of Invention ("Test Strips")

The Whitening Strips of the Invention were also evaluated for effectiveness in whitening/brightening stained dental enamel and stained Dental Restorations made of porcelain and composite materials, and compared to commercial whitening strips, Crest® 3D Whitening Strips ("Prior Art Strips"). As detailed below, similar (no statistical difference, $p>0.05$) outcomes/results were observed (in terms of desired color change) for both the Test and Prior Art Strips.

Twenty previously-extracted (20) teeth, classified as healthy by an experienced dentist using a loupe and headlamp, were selected and sterilized. By "healthy" is meant the teeth did not have any Dental Restorations or exhibit structural damage (e.g., pitting, enamel decay).

Two chips (i.e., a pair) were created from each tooth. Each chip had an approximate size of 5 mm×5 mm×3 mm in size. An impermeable plastic was affixed to the cut surfaces of the chips. Each pair was stained in a separate vial by immersion in a concentrated black tea solution "overnight" (for about 12 hours). The concentrated black tea solution was produced by steeping 2 teabags (LIPTON'S® yellow label black tea) in ½ cup of boiling water for 30 minutes. After staining, two (2) groups—Group I and Group II—were created. Each group consisted of ten pairs—A and B.

Effect of Whitening Strips of Invention on Dental Enamel

Chips in Group 1A were treated with a Test Strips. Chips in Group 1B were treated with Prior Art Strips. By "treated" is meant a whitening strip was applied to the chip for 60 minutes; thereafter, the chips were immersed in a saliva solution for approximately one (1) minute. The saliva solution was collected "fresh", without stimulation, and was filtered to remove particulate matter. The above procedure was repeated a total of ten (10) times.

At baseline (after staining but prior to the first treatment), and after each treatment (as defined below), L* and b* values were recorded using a reflectance spectrophotometer colorimeter (PCE-CSM 1, PCE Instrumentation, Alicante, Spain). Chips were photographed individually under standardized lighting conditions at each study time point.

Treatment with the Test Strip whitened the enamel surface of the chips, but had no visible effect on the underlying dentin. Mean standard deviation of L* was 9%. With the exception of T=8 hours (when b* for Test Strips was higher, and therefore, better than Prior Art Strips) differences in b* were not statististically significantly ($p>0.05$). (Because the difference at T=8 hours barely exceeded the mean standard deviation, this data point was viewed as a minor outlier.)

Effect of Whitening Mouthwash of Invention on Dental Enamel

Chips in Group 2A were treated with a Test Mouthwash. Chips in Group 2B were treated with Prior Art Mouthwash. By "treated" is meant immersion for about one minute in either the Test Mouthwash or the Prior Art Mouthwash; thereafter, the chips were immersed in a fresh saliva solution as described above for approximately one (1) minute. The above procedure was repeated a total of ten (10) times. Each treatment (i.e., immersion) with a mouthwash is viewed as the clinical equivalent of use for thirty (30) consecutive days at the recommended dose administered (rinsed) twice daily, each administration having a duration of 1 minute.

Colorimetry and clinical photographs were taken at the following time points: baseline (T=0), and the following seven time points post-immersion: 1 hour; 2 hours; 3 hours; 6 hours; 12 hours; 24 hours; 48 hours. Chips were photographed individually under standardized lighting conditions at each study time point.

Baseline b* values for the 2 groups did not differ significantly ($p>0.05$). Except as noted below, there were no statistically significant differences ($p>0.05$), between the effects of treatment with the Test and Prior Art Mouthwash formulations were statistically identical over the entire test period except at 6 h and 48 h. At 6 hours, chips treated with the Prior Art Mouthwash showed a somewhat greater shift to a yellow hue. At 48 hours, chips treated with the Test Mouthwash showed a somewhat more yellow.

Baseline L* values for Groups 2A and 2B did not differ significantly ($p>0.05$). The efficacy of the Test Mouthwash and the Prior Art Mouthwash in terms of lightening did not differ significantly over the first three hours ($p>0.05$). The maximum effectiveness of the Test Mouthwash was observed after about 1 hour of treatment. Increased treatment time was observed to add approximately 6% of additional lightening effect.

Effects of Whitening Strips of Invention on Dental Restorations

As used in the present application the term "Dental Restoration" is to be understood to mean bridges, crowns, veneers, inlays, and onlays made of porcelain or composite resin.

Dental Restorations from fourteen (14) different manufacturers/suppliers—six (6) constructed from porcelain and eight (8) from composite materials—were used to prepare chips having an approximate dimension 3 mm×2 mm×1 mm. 30 chips from the same supplier were mounted on three handling strips, each handling strip consisting of ten chips. All chips were stained by immersion in a concentrated black tea solution produced by steeping 2 teabags (LIPTON's® yellow label black tea) in ½ cup of boiling water for 2 hours.

One handling strip served as a control, and was stored in water at temperature of 4° C. and 100% humidity, and protected from ambient light in a sealed and labeled double-walled container. The remaining two handling strips (also referred to below as "active intervention") underwent "treatment", i.e., application of either a Test Strip or a Prior Art Strip to the chips for 60 minutes and, thereafter, immersion in a saliva solution (as described above in Example 1) for approximately one (1) minute. Prior to treatment, the active intervention handling strips were stored in a 0.5% chloramine-T solution for 48 hours prior to start of the study.

At baseline (time=0) and the following seven (7) specific time points, each measured from baseline, the surface structure of each sample was examined by light microscopy [Olympus® Cap Optical SZX Light Microscope (Center Valley, Pa.), at 35× magnification) to determine changes in the chip surface, and specifically to identify cracking, pitting, dissolution, roughening or erosion: 1 hour, 3 hours, 6 hours, 9 hours, 12 hours, 18 hours, 24 hours. No visible surface damage was observed in any of the samples. Representative photomicrographs are shown in FIGS. 1A (composite sample) and 1B (porcelain sample).

In addition, the color of each chip was measured by reflectance spectrophotometer (PCE-CSM 1, PCE Instrumentation (Alicante, Spain) D-65 standard illuminant; 4 mm diameter measuring area) and photographed under standard lighting conditions (i.e., the same lighting conditions were used throughout the study).

Color changes (e.g., lightening) were observed in both the Test Strips and Prior Art Strips, with no statistically significant difference between the groups; there was no difference between the control and the test groups at any time point, based on two-way ANOVA followed by Bonferroni post-test $P>0.05$.

Evaluation of Surface Changes in Porcelain and Composite Materials

Surface changes in Dental Restorations were examined by Light Microscopy, Scanning Electron Microscopy (SEM), and Profilometry.

126 chips from the control and treatment groups were examined for surface damage—cracks, pits or fissures—under light microscopy (Olympus® Cap Optical SZX Light Microscope) at three different magnifications: 10×, 25× and 35. No surface damage was observed in either the treatment groups (when compared to the controls) regardless of color, material and exposure duration.

Approximately half of the active intervention chips, and an equal amount of control chips, were affixed to Aluminum specimen mount disks using colloidal silver liquid (Ted Pella, Inc., Redding, Calif.) and coated with 9.31 nm thick gold alloy. Samples were photographed using a Scanning Electron Microscope (SEM) [FEI Magellan 400L FE-SEM, Nanolab Technologies, Inc. (Milpitas, Calif.)] at three (3) magnifications (500×, 1000× and 3000×).

Chips in treatment and control groups were compared to determine the extent of microstructural surface (if any) by a blinded, evaluator with experience and training in evaluating enamel and dental restorations using SEM. The chips were scored as "mild", "moderate" or "severe". Mild: small, individual, non-connected minor pitting or roughening covering less than 10% of the sample surface. Moderate: individual or connected pitting or roughening covering less than 25% of the sample surface. Severe: widespread pitting or roughness covering more than 25% of the sample surface. At magnifications of from 500× to 3,000×, greater surface roughening was consistently observed in composite and porcelain chips treated with Prior Art Strips than those treated with Test Strips.

The remaining half of the active intervention chips, and an equal amount of control chips, were examined by Profilometry (Perthometer M2, Mahr GmbH; Gottingen, Germany with the following specifications and calibration was used for measuring surface roughness of chips: profilometer tip diameter=2.4 mm; accuracy=0.5 mm/sec; measuring path=5.5 mm; cutoff value=250 μm). Five measurements were taken for each chip sample. Average surface roughness (based on five measurements) was recorded and evaluated by repeated measures of variance technique ($\alpha$=0.05); coincidences were eliminated by Duncan test. After every seventh specimen (total of 35 measurements), the profilometer was recalibrated. Based on profilometry, significant increases in post-whitening roughness (ANOVA, $P>0.05$) were observed in composite chips treated with Prior Art Strips, but not in composite chips treated with Test Strips. No significant increases in post-whitening roughness (ANOVA, $P>0.05$) were observed in porcelain chips treated with Test Strips and Prior Art Strips.

Effect of Mouthwash of Invention on Remineralization 10 healthy volunteers (7 females and 3 males), ages 18-45, each with a minimum of 16 clinically and radiographically healthy teeth as defined by clinical examination, and with an absence of any apparent pathology, were recruited to participate in a randomized, double-blind clinical study with three study arms (i.e., segment), each lasting five days. The study objective was to compare remineralization of eroded (i.e., "demineralized") enamel by use of two mouthwashes: (i) the mouthwash of the present invention ("Mouthwash of Invention"); and (ii) a prior art mouthwash, Sensodyne® Pronamel® Flouride Rinse ("Prior Art Mouthwash") containing, as an active ingredient, sodium fluoride at a concentration of 0.05% (0.02% w/v fluoride ion).

Three hundred (300) enamel chips were created from extracted teeth classified as healthy were extracted by an experienced dentist. More particularly, 150 pairs of chips were cut from the same area of each extracted tooth. A first group of 150 chips (one from each pair) were eroded by 6-hour immersion in 40 ml of an acidic solution (buffered to pH of approximately 4.4) as described by Stookey G K, et al. "The Featherstone laboratory pH cycling model: a prospective, multi-site validation exercise" *Am. J. Dent.* Vol. 24, No. 5, pp. 322-328 (2011) (2.0 mmol/l calcium, 2.0 mmol/l phosphate, and 75 mmol/l acetate). A second group of 150 chips (the corresponding/remaining tooth from each pair) was designated as controls, and stored in sealed double-walled containers, impervious to ambient light, in de-mineralized water at a temperature of 4° C. and 100% humidity.

Thirty (30) intra-oral retainers were fabricated from standard alginate impressions of the upper teeth)—three for each study participant. Five enamel chips from the first group, eroded as described above, were attached to the palatal area of each retainer; the chips were spaced approximately 0.75 to 1.5 cm apart. A new retainer was made prior to each of the three study segments.

Total study duration was 36 days:
Days 0-7: one-week washout period
Days 8 through 12: Study Segment 1 (intra-oral retainer worn; no mouthwash)
Days 13-19: one-week washout period
Days 20-24: Study Segment 2 (intra-oral retainer worn; Mouthwash of Invention used)
Days 25-31: one-week washout period
Days 32-36: Study Segment 3 (intra-oral retainer worn; Prior Art Mouthwash used)

Subjects were supplied with toothpaste (Crest® Total Care, Procter & Gamble, Cincinnati, Ohio) in a quantity sufficient to brush their teeth twice daily for the duration of the study (36 days) as well as with a new soft bristled toothbrush (Oral B®, GSK, Warren, N.J.) at the outset of the study (Day 0) and at beginning of the second and third study segments (Study Days 20 and 32). Subjects were instructed not to use any oral care products (e.g., floss or baking soda) other than those provided by the study staff.

Throughout the study—from the initial washout period through completion of Study Segment 3—participants (i) brushed their teeth twice daily, each time for two minutes, and (ii) wore the retainers for a minimum of 22 hours per day. Neither the retainer nor the enamel specimens were brushed. Retainers were removed when eating solid foods; at which time the retainers were placed in a sealed container. Subject compliance (wearing of retainers for 22 hours/day) was confirmed by diary entries completed on a daily basis.

For Segment 2, subjects were randomly assigned mouthwash either the Mouthwash of the Invention or Prior Art Mouthwash. For Segment 3, subjects were assigned the other mouthwash. Subjects that used Mouthwash of the Invention in Segment 2, used the Prior Art Mouthwash in Segment 3. Subjects that used the Prior Art Mouthwash in Segment 2, used the Mouthwash of the Invention in Segment 3.

In both Segments 2 and 3, after each brushing, participants rinsed with the assigned mouthwash for sixty seconds; thereafter, the mouthwash was expectorated. For thirty minutes following expectoration, subjects did not rinse, drink or eat.

At the end of each segment, a total of fifty enamel chips were collected (five chips from the retainers worn by each of the ten study participants) and were tested for microindentation hardness (also known in the art, and referred to in this application, as "microhardness"); fifty controls were tested at the same time. More particularly, three microhardness measurements were taken on each chip using the Knoop test, an established and standard technique for measuring enamel mineralization, by applying a fixed force (load) using a pyramid-shaped diamond indenter for a specified dwell time period: one in an area of "typical" appearance; one in an area with the healthiest ("best") appearance; and one in an area with the most damaged ("worst") appearance. See, ASTM Standard E384-16 (ASTM International, West Conshohocken, Pa.). See also, Craig R G and Peyton F A, "The Microhardness of Enamel and Dentin" J Dent Res, Vol. 37, No. 4, pp. 661-668 (1958). Microhardness measurements were compared using the Kruskal-Wallis one-way analysis of variance with post-hoc Tukey's test.

The microhardness of the eroded (i.e., demineralized) enamel chips in Segments 2 and 3 was substantially the same. There were no statistically significant differences ($p>0.05$) between microhardness of enamel chips treated (i.e., rinsed) with the Mouthwash of the Invention and the Prior Art Mouthwash. Put differently, demineralized enamel chips were observed to have substantially "regained" their original microhardness after rinsing with both mouthwashes.

In Vivo Effects of Whitening Strip of Invention on Tooth Sensitivity and Gingival Irritation Ten participants ages 18-45 (mean 29.4 years)—each with (i) a minimum of 16 clinically and radiographically healthy teeth, as determined by clinical examination and (ii) an absence of any pathological symptoms, gingival recession or tooth sensitivity prior to enrollment—were recruited to participate in a 10-day, randomized, double-blinded, clinical study.

At the commencement of the study, each subject received forty (40) identically packaged, coded whitening strips—20 Test Strips (as defined above) and 20 Prior Art Strips (as defined above)—as well as a new soft-bristled Oral B® toothbrush and Crest Total Care® toothpaste. Subjects brushed their teeth twice daily and used only the oral hygiene products as described above. For example, no mouthwash or floss was used. Subjects applied four whitening strips—one on each designated quadrant of the mouth (i.e., upper left, lower left, upper right, lower right)—to the outer surface of the teeth for thirty (30) minutes each day. After treatment, subject rinsed their mouths with water. Subjects were instructed to wait at least 22 hours before each subsequent application. After each application, on a daily basis, subjects completed a questionnaire to report tooth sensitivity using the 5-point Likert Scale, and gingival irritation (yes or no). At the conclusion of the study, cumulative self-reported scores were calculated for both endpoints—tooth sensitivity and gingival irritation. Additionally, the two endpoints were evaluated at baseline, and on Study Days 5 and 10 by a blinded clinician. Sensitivity was measured (yes/no) after a 3 second burst of pressurized air. Gingival irritation was determined by visual inspection on a scale ranging from 0 to 3.

Quadrants of the oral cavity to which the Test Strips were applied were reported to have lower levels of gingival irritation. Sensitivity was reported to be comparable in the two treatment groups, both as evaluated in home and by a trained observer (in office clinical evaluation at baseline and on Days 5 and 10.

Reduction in Plaque Presence and Gingival Health

Ten subjects who had received professional prophylaxis within 4-6 weeks prior to the beginning of the study, and abstained from oral hygiene on the lower anterior teeth for 3 days. Plaque levels (Turesky Modification of Quigley-Hein Index ("PI"), gingival inflammation (Löe and Silness Gingival Index ("GI"), and sulcus bleeding ("mSBI") were recorded before and after cessation of oral hygiene measures.

Participants were randomized with regard to sequence of twice daily 1 min use of a mouthwash of the present invention, a control mouthwash and no mouthwash while abstaining from brushing the lower anterior teeth. GI, PI and mSBI were recorded before and after each 3-day long arm. During the one week wash out period between each study arm, subjects brushed with Crest® Pro-Health™ toothpaste (Procter and Gamble, Cincinnati, Ohio) using a new Oral B® Pro-Flex™ toothbrush (Procter and Gamble, Cincinnati, Ohio) for each washout period of the study. Use of any other oral hygiene measures was not permitted, included chewing gum All investigators and subjects were blinded with regard to the mouthwash allocation. At each visit, subjects were questioned about any potential adverse effects of any products. 24-hour telephone contact information was provided to all subjects in case of any emergencies.

Plaque was scored on a scale of 0 to 5 according to the Turesky modification of the Quigley-Hein Plaque Index. Gingival health was evaluated using the Löe-Silness Gingival Index (0-3) and the Sulcus Bleeding Index.

In order to evaluate the data, the difference between endpoint and baseline value for each parameter was determined for each subject. Using a 2-sided T-test and standard statistical approaches for crossover studies, the clinical indices at study end were compared between (a) mouthwash of the invention and control mouthwash and (b) mouthwash of the invention vs no mouthwash.

Figure 1:
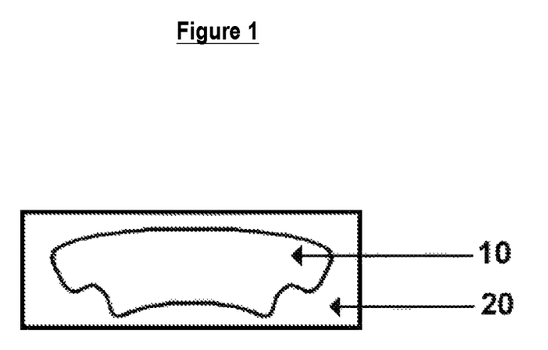
FIG. 1 illustrates an embodiment of the whitening strip of the present invention [10] attached to a release liner [20]. This embodiment is configured to be applied to the bottom row of teeth.
Figure 2:
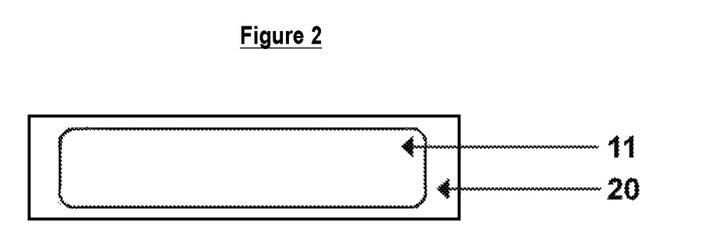
FIG. 2 illustrates an embodiment of the whitening strip of the present invention [11] attached to a release liner [20]. This embodiment is configured to be applied to the top row of teeth.

At study outset and after 3 days of abstaining from oral hygiene, the clinical indices did not differ significantly between all subjects (FIGS. 1-3). None of the data showed any evidence of a significant carryover effect from the first arm to the second (p>0.186). For all of the clinical indices measured, the mouthwash of the invention effects did not differ significantly from those of the control mouthwash (p>0.164). Both mouthwashes removed plaque and maintained gingival health more effectively than when no mouthwash was used (p<0.05).

The crossover study design that was used in this research is valid where there is minimal carry over effects. Our data confirm that this was indeed the case in this study. In order to further overcome any potential effects of the sequential crossover design of this study, the sequence of mouthwash usage was randomized so that 3 subjects used the mouthwash of the invention first, 3 subjects used the control mouthwash first, and 4 subjects used no mouthwash at all first. Overall, during the 8-week study period, oral health improved in both groups using the mouthwash.

Three-day use of the mouthwash of the invention or the control mouthwash reduced plaque presence and gingival inflammation to a very similar degree. Plaque indices were reduced by approximately 30% after 3-day use of either mouthwash, whereas plaque levels increased by approx. 25% when no mouthwash was used. Gingival indices and BOP were significantly reduced after use of either mouthwash, whereas they increased significantly in the absence of a mouthwash regimen.

Comparative Study of Mouthwash of Invention on Oral Biofilm, pH Buffering, Dry Mouth, and Gingival Health A 3-leg study was conducted on ten patients each of whom was clinically diagnosed with xerostomia. In two legs, subjects used a test or control product for xerostomia intervention; in the third leg, they used no intervention for xerostomia. The "test product" was a mouthwash of the invention as described above and formulated for use in the treatment of dry mouth. The control product was Biotene™ Dry Mouth Oral Rinse.

The study aims were as follows:
(i) Use 2-Tone disclosing solution combined with digital photography and image analysis to quantify biofilm presence at baseline and after 7-day use of a test and a control product, each vs no xerostomia treatment product with a 1-week washout between the 3 legs of the study.
(ii) Use conventional clinical indices (PI, mSBI, GI) to quantify gingival health at baseline and after 7-day use of a test and a control product vs no xerostomia treatment product with a 1-week washout between the 3 legs of the study.
(iii) Quantify salivary volume, pH and pH-buffering performance at baseline and after each 7-day study leg.
(iv) Document subject self-evaluation of dentinal sensitivity at baseline and after 7-day use of a test product and a control agen vs no xerostomia treatment product with a 1-week washout between each of the 3 legs of the study.
(v) Document subject self-evaluation for dry mouth using a standardized questionnaire at baseline and after 7-day use of a test product and a control product vs no xerostomia treatment product with a 1-week washout between the 3 legs of the study Subjects were randomized with regard to sequence of the 3 legs of the study. Subjects also underwent plaque staining and standardized photography at baseline and at the end of each study leg. Digital image analysis was performed to identify plaque age (color-based) and surface coverage in the oral cavity. Plaque Index (PI), Gingival Index (GI) and Sulcus Bleeding Index (mSBI) were recorded at baseline and at the end of each study leg to provide a quantitative measure of gingival health. Salivary volume, pH and buffering capacity were determined by asking the subject to pool saliva in the floor of their mouth for a 5-minute duration, then expectorate the saliva into a sterile collecting cup. During the leg incorporating test and control product use, subjects rinsed with the test/control product. Saliva pooling/expectoration were collected twice, at t=10 and t=40 mins. During the "no test product" leg, subjects rinsed with water instead. Additionally, subjects completed a standardized self-evaluation questionnaire for dry mouth and dentinal sensitivity at each visit.

The following results were observed:

There was a significant reduction in old and new plaque presence after use of test or control products for 1 week vs no product (p<0.05). Old and new plaque levels were similar for the test and the control products (p>0.1). Old plaque presence fell to approximately 50% of the baseline value, while new plaque presence was reduced to approximately 60% of the baseline level.

There was a significant reduction in clinical Plaque Index by approx. 60% after use of test or control products for 1 week (p<0.05). Generally clinical indices were similar for the test and the control products (p>0.1). The reduction in Gingival Index after 7 Days of test or control product use almost reached a significant level (p=0.0563 for test product, p=0.0643 for control product). All other values did not change significantly during the course of this study.

Saliva volume doubled at the end of the test and control study legs, representing a statistically significant increase in each case (p<0.05). In the study leg with no intervention, saliva production did not change significantly (p>0.1).

PH values did not differ significantly between study legs and time-points (p>0.05).

The invention claimed is:
1. A method for visibly whitening teeth at least three shades as measured using a tooth shade grading system comprising the step of administering for at least 30 seconds at least once daily an oral care product that is a dentifrice or a mouthwash that does not contain a fluoride source and consists essentially of
   a. Dead Sea salt at a concentration of from 0.5% to 1.5% by weight of the dentrifice
   b. aloe vera juice at a concentration of at least 40%;
   c. xylitol at a concentration of at least 7.5%; and
   d. coconut oil;
   e. one or more essential oils selected from the group consisting of:
      (i) essential oil of wintergreen at a concentration of up to 1%,
      (ii) essential oil of peppermint at a concentration of up to 0.05%, and

(iii) essential oil of spearmint at a concentration of up to 1%, wherein the method reduces plaque buildup by at least 10% as measured on the Quigley-Hein Plaque Index.

2. The method according to claim 1 wherein the oral care product contains an essential oil of sage or essential oil of lemon peel.

3. The method according to claim 1 wherein the oral care product is a dentrifice that contains at least one surfactant that is not sodium lauryl sulfate or sodium laureth sulfate.

4. The method according to claim 3 wherein the at least one surfactant is sodium methyl cocoyl taurate.

5. The method of claim 1 wherein gingival inflammation is reduced by at least 25% as measured on the Loe-Silness gingival index.

6. The method of claim 1 wherein dentine sensitivity is reduced after a 3 second burst of pressurized air as measured on a 5-point Likert scale.

7. The method of claim 1 wherein the oral care product is non-cytotoxic within the framework of ISO test method 10993-5 for biological evaluation of in vitro cytotoxicity.

8. The method of claim 1 wherein the oral care product is administered at least twice daily, each administration for at least 30 seconds.

9. The method of claim 1 wherein the oral care product is administered for at least 60 seconds, at least once daily.

10. The method of claim 1 wherein the oral care product is administered for at least 60 seconds, at least twice daily.

\* \* \* \* \*